(12) United States Patent
Sukavaneshvar et al.

(10) Patent No.: US 7,906,338 B2
(45) Date of Patent: *Mar. 15, 2011

(54) SYSTEMS AND METHODS FOR MEASURING FLUID PROPERTIES

(75) Inventors: Sivaprasad Sukavaneshvar, Salt Lake City, UT (US); Johnny Rhodes, Draper, UT (US); Ramachandran Thekkedath, Salt Lake City, UT (US)

(73) Assignee: Thrombodyne, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/214,544

(22) Filed: Jun. 18, 2008

(65) Prior Publication Data
US 2009/0162885 A1 Jun. 25, 2009

Related U.S. Application Data

(63) Continuation of application No. 11/504,970, filed on Aug. 15, 2006, now Pat. No. 7,393,690, which is a continuation-in-part of application No. 10/431,358, filed on May 6, 2003, now Pat. No. 7,262,059.

(51) Int. Cl.
*G01N 33/86* (2006.01)
(52) U.S. Cl. ............... 436/69; 436/63; 436/52; 436/164; 436/165; 422/73; 422/81; 422/82.05; 422/82.09; 435/2; 435/287.1; 435/288.7
(58) Field of Classification Search ............... 422/73, 422/81, 82.05, 82.09, 99, 102; 436/63, 69, 436/52, 164, 165; 435/2, 13, 29, 287.1, 288.7
See application file for complete search history.

(56) References Cited

U.S. PATENT DOCUMENTS

| | | | |
|---|---|---|---|
| 4,936,674 A | 6/1990 | Ikeda et al. |
| 4,964,728 A | 10/1990 | Kloth et al. |
| 5,061,381 A | 10/1991 | Burd |
| 5,325,295 A | 6/1994 | Fratantoni et al. |
| 5,352,413 A | 10/1994 | Kratzer et al. |
| 5,523,238 A | 6/1996 | Varon et al. |
| 5,907,399 A | 5/1999 | Shirasawa et al. |
| 6,043,871 A | 3/2000 | Solen et al. |
| 6,773,923 B2 | 8/2004 | Patzke |

(Continued)

FOREIGN PATENT DOCUMENTS
DE 19939252 4/2001
(Continued)

OTHER PUBLICATIONS

Hall, Matthew et al., "Formation of Occlusive Platelet Aggregates in Whole Blood Caused by Low Concentrations of ADP" ASAIO, Journal 2000, pp. 593-695.

(Continued)

*Primary Examiner* — Maureen M Wallenhorst
(74) *Attorney, Agent, or Firm* — Thorpe North & Western LLP

(57) ABSTRACT

A fluid property measurement system for measuring free stream particulates includes a fluid movement device positioned within a fluid container which is configured to cause fluid flow within the fluid container along a fluid flow path when a fluid is present. A constricted region along the fluid flow path generates a region of concentrated streamlined flow within the constricted region and mixing of the fluid outside of the constricted region. A property measuring device is positioned with respect to the constricted region to measure fluid properties in the region of streamlined flow.

41 Claims, 5 Drawing Sheets

U.S. PATENT DOCUMENTS

| | | | |
|---|---|---|---|
| 7,037,428 | B1 | 5/2006 | Robinson et al. |
| 7,262,059 | B2 | 8/2007 | Zheng et al. |
| 7,393,690 | B2 | 7/2008 | Sukavaneshvar et al. |
| 2003/0096423 | A1 | 5/2003 | Ryan et al. |
| 2004/0166551 | A1 | 8/2004 | Moulds et al. |
| 2004/0224419 | A1 | 11/2004 | Zheng et al. |
| 2005/0196748 | A1 | 9/2005 | Ericson |
| 2006/0269978 | A1 | 11/2006 | Haworth et al. |

FOREIGN PATENT DOCUMENTS

| | | |
|---|---|---|
| JP | 5-240863 | 9/1993 |
| WO | WO 9908107 | 2/1999 |

OTHER PUBLICATIONS

Xia, Zheming et al., "Aggregation Efficiency of Activated Normal of Fixed Platelets ina Simple Shear Field: Effect of Shear and Fibrinogen Occupancy" Biophysical Journal, vol. 55, Jun. 3, 1994, pp. 2190-2201.

Zheng, Yu et al, "The Light-Scattering Whole Blood Aggregometer" Arach Pathol Lab Med, vol. 122, Oct. 1998, pp. 880-886.

Solen, Kenneth et al., Light-Scattering Instrument to Detect Thromboemboli in Blood, Journal of Biomedical Optics, Jan. 2003, vol. 8, No. 1, pp. 70-79.

Ozaki, Yukio et al., "Detection of Platelet Aggregates with a Particel Counting Method Using Light Scatterin," Analytical Bichemisttry 218 (1994), pp. 281-294.

Sukavaneshvar, Sivaprasad et al., "Enhancement of Stent-Induced Thromboembolishm by Residual Stenoses: Contribution of Hemodynamics," Annals of Bimedical Engineering, vol. 28, 2000, pp. 182-193.

Fukuyama et al.; "Continuous measurement of Shear-Induced Platelet Aggregation"; Thrombosis Research; 1989; pp. 253-260; vol. 54, No. 3.

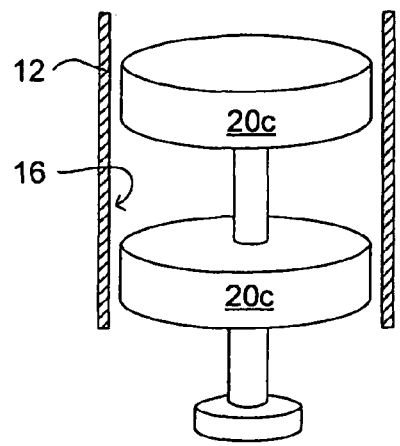
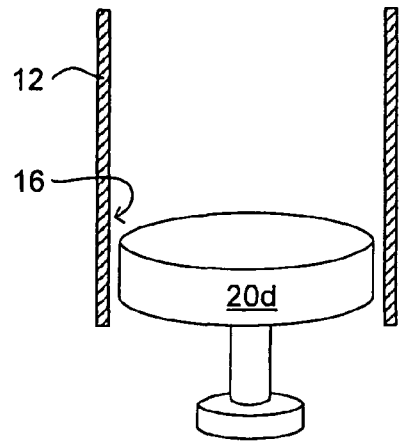
FIG. 2A        FIG. 2B
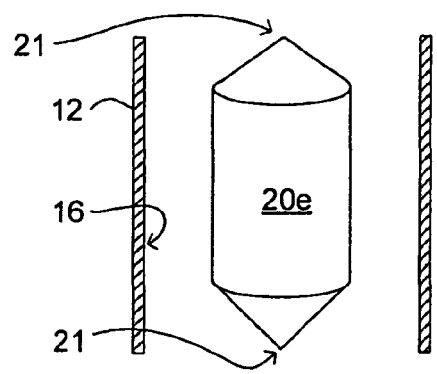
FIG. 2C
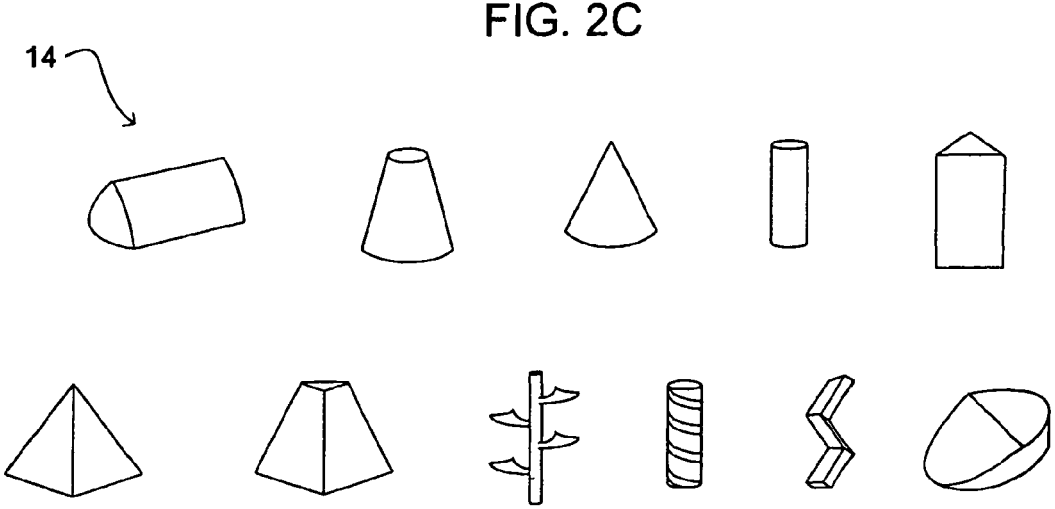
FIG. 3

SYSTEMS AND METHODS FOR MEASURING FLUID PROPERTIES

RELATED APPLICATIONS

This application is a continuation of U.S. patent application Ser. No. 11/504,970, filed Aug. 15, 2006, and now U.S. Pat. No. 7,393,690, issued Jul. 1, 2008, which is a continuation-in-part of U.S. patent application Ser. No. 10/431,358, filed on May 6, 2003, and now U.S. Pat. No. 7,262,059, issued Aug. 28, 2007, each of which is hereby incorporated herein by reference in its entirety.

FIELD OF THE INVENTION

The present invention relates generally to methods for measuring fluid properties, such as fluid suspension properties. More particularly, in one embodiment, the present invention relates to measuring blood platelet function.

BACKGROUND OF THE INVENTION

Currently, there are over 2 million hospitalizations and nearly 10 million visits to physicians that are associated with coronary heart disease in the United States every year. A majority of these patients receive some form of antiplatelet therapy, e.g. Aspirin, Plavix, etc., to prevent acute thrombosis and clotting associated with vascular interventions, such as angioplasty, or implants, such as coronary stents. Excess dosage of the antiplatelet drugs can result in bleeding complications because the platelet function is over-suppressed, while insufficient dosage can fail to prevent acute thrombosis and clotting due to insufficient suppression of platelet function. Thus, it would be valuable to assess platelet function in patients at certain points of care and adjust the antiplatelet drug dosage to the specific needs of each individual. The relevance of such a point-of-care approach is becoming increasingly important in the context of platelet GP IIb/IIIa antagonists, e.g. Abciximab, Tirofiban, Eptifibatide, etc., with short half-lives (typically about 1 hour) that can be adjusted carefully and quickly to meet the needs of each patient. Thus, an effective point-of-care platelet function assay that enables management of therapeutic regimen has considerable clinical value.

A platelet aggregometer is an instrument that can assess certain aspects of platelet function. This device can be used by starting with a platelet suspension, such as blood or platelet rich plasma, which can be collected from a patient and dispensed into a disposable sample holder of the platelet aggregometer. A chemical stimulus, such as collagen, can be added to the platelet suspension in the sample holder, and subsequent agitation/mixing of the platelet suspension with the stimulus can cause the platelets to aggregate. The characteristics of this aggregation can be measured by various methods known by those skilled in the art, and the degree of aggregation measured can be directly related to the function of the platelets.

Currently available methods in the field of platelet aggregometers include sample holders that provide thorough mixing and agitation of the platelet suspension to cause platelet aggregation. However, most of these methods and devices create flow that is not conducive to enabling certain detection modalities of platelet aggregation, particularly for light scattering methods.

Many methods utilize mechanical mixing which often damages or otherwise alters fluid characteristics. For example, the use of a roller pump has been one proposed method for moving blood. However, the compression of a flow conduit containing blood by means of rollers often disfigures platelet aggregates, damages red cells, and alter their characteristics. Thus, the ergonomics of such designs can be undesirable, and loading of the blood sample and/or the chemical stimulus that causes platelet aggregation can be cumbersome. These limitations detrimentally influence the quality and consistency of platelet aggregation, which in turn adversely affects the reproducibility and reliability of the measurement of platelet function. Other methods include designs that present relatively good flow patterns for measurement using light scattering techniques, but do not provide significant mixing that induces more thorough and consistent platelet aggregation.

SUMMARY OF THE INVENTION

It has been recognized that there is a need to develop systems and methods that provide good mixing properties, without substantial damage to blood aggregates or other fluid properties to be measured. At the same time, such a system can also provide streamlined flow in a distinct region for accurate measurement of a fluid property. The present invention addresses the limitations of previous methods and presents fluid measurement devices and methods that enable more reliable assessment of platelet function, or in the case of other fluids, more reliable assessment of a desired fluid property.

In a first embodiment, a fluid property measurement system for measuring free stream particulates can include a fluid movement device positioned within a fluid container to cause fluid flow within the fluid container along a fluid flow path. The fluid movement device can often be a rotor although other devices can also be suitable. The system can further include a constricted region along the fluid flow path which generates a region of concentrated streamlined flow within the constricted region and mixing of the fluid outside of the constricted region. A property measuring device can also be functionally positioned with respect to the constricted region to measure fluid properties in the region of streamlined flow. In one detailed aspect of the present invention, the constricted region can be formed by a stenotic baffle system. The constricted region and fluid movement device can advantageously be configured to provide free stream aggregation of material such that measurement of aggregation can be based on free stream properties.

In another embodiment of the present invention, a method for measuring free stream properties of a fluid can include placing a quantity of fluid in a container and inducing flow in the fluid. The induced flow can be substantially streamlined in at least a measuring region of the container by constricting flow. Further, the fluid can be recirculated through the measuring region. A mixing region can be created separate from the measuring region sufficient to substantially mix the fluid and a property of the fluid can be measured in the measuring region. The systems and methods of the present invention provide an improved aggregation measurement of biological fluids while also minimizing adverse affects on the fluid properties such as platelet function.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIGS. 2A, 2B, and 2C are perspective views of various rotors in accordance with embodiments of the present invention, shown within a cross-sectional view of side walls of a fluid container.

FIG. 3 is a perspective view of several representative disruption members for use in accordance with embodiments of the present invention.

Figure 1A:
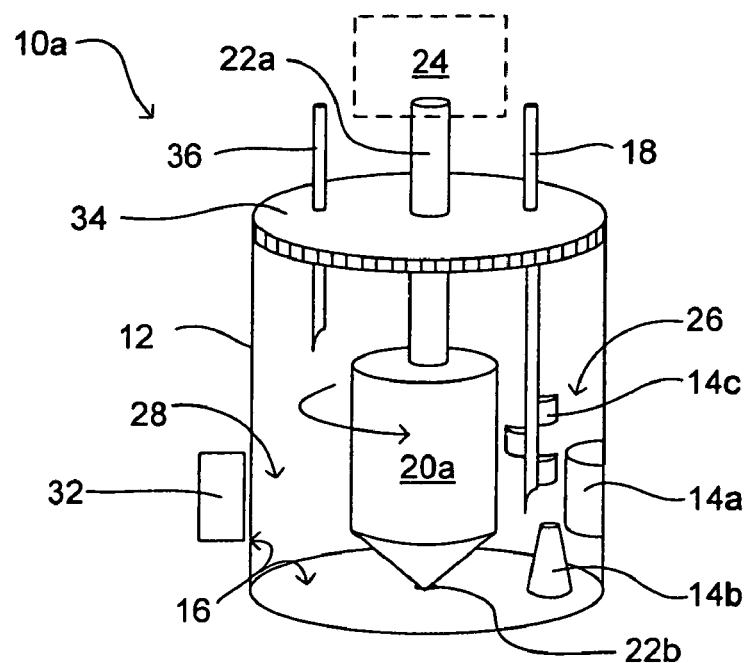
FIG. 1A is a perspective view of a fluid measurement device in accordance with an embodiment of the present invention.

The drawings are intended to illustrate several specific embodiments of the present invention and are not intended to be unnecessarily limiting. As such, departure may be had in dimensions, materials, and features while still falling within the scope of the invention.

DETAILED DESCRIPTION OF THE PREFERRED EMBODIMENT(S)

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

In describing and claiming the present invention, the following terminology will be used.

The singular forms "a," "an," and "the" include plural referents unless the context clearly dictates otherwise. Thus, for example, reference to "a rotor" includes reference to one or more of such structures, and reference to "a stimulus" includes reference to one or more of such factors.

As used herein, "recirculating," "recirculated," or "recirculation" refers to fluid flow along a path that is primarily related to a measuring region where fluid recirculation occurs, though recirculation can also occur in other non-measuring regions. By recirculating in the measuring region, a better measurement sample over a predetermined time can be taken as to the properties of the fluid. For example, in one embodiment, recirculation can occur by circumferential recirculation, and in another embodiment, the recirculation can be by bi-directional recirculation.

As used herein, "fluid" refers to a flowable composition and can include liquid, gas, suspended solid or other flowable mass. Fluids can be in the form of suspensions, emulsions, solutions, mixtures, or the like.

As used herein, "mixing" refers to disturbed flow or separated flow of a fluid. In one embodiment, the addition of a chemical stimulus can be accompanied by mixing in order to facilitate distribution of the stimulus sufficient to affect the bulk properties of the fluid. As used herein, mixing does not include mixing that is merely the result of intermolecular, intercellular, or structural forces exerted within a fluid under substantially streamlined flow, or which is solely the result of diffusion due to concentration gradients.

As used herein, "streamlined" refers to a fluid flow state that is more streamlined than is present in a mixing region acting on the same fluid. Additionally, a streamlined flow is capable of providing fluid flow dynamics such that at least a substantially accurate measurement can be taken, such as by use of a light scattering device or other fluid property measuring device. Further, streamlined flow typically refers to minimally disturbed flow that can be predominantly laminar, including arcuate flow in case of a cylindrical container. Such flow is suitable for testing using methods such as light scattering, etc. Although a common definition of the term "streamlined" can define a path or paths characterized by a moving particle in a fluid such that the tangent to the path at every point is in the direction of the velocity flow, the term as used herein is intended to be broader in scope to include flow that is minimally disturbed such that more accurate readings using fluid measuring equipment can be used, e.g., light scattering particle detection devices.

As used herein, "free stream particulates" refers to masses which are non-liquid materials contained within a fluid which are not attached to a fixed structure such as a container wall or other solid member. Free stream particulates can include, but are not limited to, platelet aggregates, solid debris, air bubbles, clots, and the like.

As used herein, "stenotic" refers to any constriction or narrowing of a fluid flow path. Typically, stenotic baffles can have a gradually narrowing portion which leads to a flow path portion having substantially constant cross-sectional area, and a subsequent expanding portion where cross-sectional area gradually increases to an unobstructed flow.

As used herein, the term "concentrated" when referring to streamlined flow, indicates that a greater number of streamlines per unit area are present than are present in other areas of the system in accordance with embodiments of the present invention. Areas outside of where there is "concentrated" streamline flow can be from streamlined (though less concentrated) to chaotic.

As used herein "fluid dynamic focus," "fluid dynamically focused," or the like, refers to fluid conditions where elements of the fluid are can become concentrated in a smaller cross-sectional area of controlled volume of flow.

Concentrations, amounts, and other numerical data can be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. Further, such an interpretation should apply regardless of the breadth of the range or the characteristic being described.

As illustrated in FIG. 1A, a system, indicated generally at 10a, in accordance with embodiments of the present invention, is shown for measuring a property of a fluid. A variety of fluids can be suitable for measurement using the method of the present invention. Suitable fluids include, but are not limited to, physiological fluids such as platelet suspensions, platelet rich plasma, whole blood, leukocyte suspensions, erythrocyte suspensions, plasma, red blood cell suspensions, urine, bile, etc. Additionally, physiologically compatible fluids, such as saline, or immiscible fluids, such as oils (with water based fluids) can be added to a fluid to be measured for a desired purpose. In one embodiment, these or other fluids can contain exogenous additives such as polymer microbeads, cells, powders, or combinations thereof. These additives can facilitate measurement or otherwise affect the fluid so as to improve handling and/or measurement. Other non-physiological fluids such as coal and other slurries can also be contained and assessed using the sample holder described herein. The following description and examples are described using a platelet suspension or other blood component-containing fluid, such as whole blood. This has been done for convenience, and is only an example of one of the types of fluid that can be used with the present invention.

In accordance with one aspect of the present invention, a fluid container 12 is configured for recirculating fluid. The fluid container can be shaped so as to allow fluid to circulate within the container recursively. The fluid flows unidirectionally in a substantially circular pattern in FIGS. 1A, 1B, and 5A-C, however any recirculating flow can be used in accordance with embodiments of the present invention, such as bi-directional recirculating flow as is described in FIGS. 4A and 4B, discussed below. In one aspect of the invention, the fluid container can provide for an essentially batch process wherein fluid is introduced into the container either in a single charge or incrementally. In either embodiment, the flow of the fluid inside the container generally follows a recirculating path through the same region or regions.

Returning to discussion of FIG. 1A, in accordance with one aspect of the present invention, the fluid container 12 can be comprised of any material that is compatible with a chosen fluid to be mixed and a property measured. Additionally, the fluid container 12 can be configured to facilitate measurement of various properties using known methods. For example, if the fluid container were intended for use with a light scattering whole blood platelet aggregometer (LSWBPA), the container that holds the fluid can be made of transparent or translucent materials that permit passage of light through the container walls and into the fluid. Many plastics such as, but not limited to, polycarbonates, polyacrylates, polystyrenes, polyvinylchlorides, polyurethanes, and other polymeric materials, fulfill these criteria. Glass can also be acceptable depending on the fluid and duration of exposure to the fluid. Typically, when the fluid is a blood component-containing fluid, the fluid container can be formed of a relatively small size that is capable of handling very small volumes of fluid. In one aspect of the present invention, the fluid container has a volume of less than 10 ml, while an internal volume of less than about 2 ml is sufficient. One current embodiment of the present invention has an internal fluid capacity from about 0.05 ml to 0.5 ml. Generally, the fluid containers can have a volume from about 0.02 ml to about 30 ml.

In another aspect of the present invention, a measuring region or streamlined flow region 28 is provided distinct from a mixing region 26. The measuring region 28 is configured for providing substantially streamlined flow of the fluid within the fluid container 12. Flow of fluid within the container 12 can be induced by a method that is non-destructive of the fluid or its properties. Such methods include the use of a rotor 20a, other mixer (not shown), stir bar (not shown), forced flow device (not shown), or an external drive (not shown). These and other means for inducing flow can also be suitable for use in the present invention, but should provide a streamlined region 28, and should not adversely affect the fluid properties. Preferred methods for inducing flow in a blood component-containing fluid will not damage aggregates, destroy coagulated masses, or otherwise adversely affect the blood components, such as by causing significant hemolysis.

In this embodiment, the rotor 20a is a cylindrical body having a conical portion at a bottom end. The rotor can be rotated and secured using shaft 22a and cavity 22b system. The shaft 22a can be coupled to a constant or variable speed motor 24 that can be used to adjust the rotational speed based on the fluid properties, such as viscosity or fragility. Depending on the viscosity of the fluid, the rotor speed can vary from one medium to another, while the rotor 20a is being driven by non-varying force. In some scenarios, it may be desirable to maintain the rotor speed at a particular value. This can be accomplished by either using a large driving force to drive the rotor 20a, or by providing a motor 24 equipped with a feedback control to either increase or decrease the rotor driving force by means of monitoring the rotor speed. This embodiment generates general circumferential recirculation of the fluid within the system.

As mentioned, the fluid container 12 includes a mixing region 26 configured for substantial mixing of the fluid in the fluid container. The mixing region 26 is a region within the container 12 in which the fluid is mixed, and which is separate from a measuring or streamlined flow region 28. The mixing that can occur in the mixing region 26 can be turbulent or more gentle in action, but should be sufficient to substantially mix or homogenize the composition of the entire fluid. Thus, the measurement of fluid properties in the separate measuring region 28 can be representative of the bulk properties of the fluid. The separation of mixing region 26 and measuring region 28 allows for increased control of the fluid flow environment, and improves the ability to prevent damage to the fluid. The mixing region 26 can be produced using a variety of disruption members 14a, 14b, and/or 14c, such as a stationary obstruction, movable obstruction, rotating mixer, vagile object, or combinations thereof. These disruption members can cause a local disruption or turbulence in the streamline flow of the fluid sufficient to mix the fluid.

In one aspect of the present invention, the disruption members 14a, 14b, 14c protrude from an inside surface 16 of the fluid container 12. The disruption members 14a, 14b, 14c can be molded as an integral part of the container, or can be separately formed members. Additionally, the disruption members 14a, 14b, 14c can be attached to the inner surface 16 in a permanent or removable manner. FIG. 1A shows disruption members 14a and 14c as stationary obstructions affixed to the inner surface 16 side walls of the fluid container 12. Disruption member 14c is also shown wherein baffles are affixed to an elongated rod member 18. The rod member 18 can be a rotating or fixed shaft, or a hollow tube inlet for introducing fluid or other material into the fluid container. Disruption member 14b is a stationary obstruction affixed to the inner surface 16 bottom of the fluid container 12.

One or more disruption member 14a, 14b, 14c can affect mixing in the mixing region 26 in the vicinity of the one or more member 14a, 14b, 14c. Three different disrupting members are shown for exemplary purposes only. One disrupting member is typically sufficient to provide disturbed flow, or even turbulent flow, though more than one can be present at or near the mixing region 26 in some embodiments.

The mixing region 26 can vary in size depending on such variables as the fluid flow velocity approaching the disruption members, fluid viscosity, and the particular shape of the disruption member(s). Often a single disruption member and mixing region is sufficient to produce substantial mixing of the fluid. However, as shown in FIG. 1A, multiple mixing regions can be present.

In one embodiment, the surfaces that contact the fluid, i.e., rotor 20a and/or inside surface 16, can be configured to be highly compatible with the introduced fluid, and can also be configured to avoid contamination of the fluid and/or deterioration of the surfaces. For example, the fluid container 12, if made for use with platelet suspensions, can be made of materials that are generally compatible with the platelet suspension. Additionally, it may be desirable for aggregates not to adhere to surfaces within the apparatus or system 10a, such as the inner surface 16 of the fluid container 12, the rotor 20a, the disruption member(s) 14a, 14b, 14c, or other parts of the apparatus. This can be accomplished by using smooth geometries in the apparatus and/or coatings, such as lubricious, hydrophilic, or hydrophobic coatings on the apparatus components. Such coatings, if used, can increase biocompatibility and/or decrease friction and associated adherence to the coated surfaces. Coatings suitable for use in the present invention can include, but are not limited to, hydrophilic, hydrophobic, lubricious, heparin, carbon-diamond, or ceramic coatings.

In addition to the above components, the fluid container 12 can have a cap 34 to hold the fluid within the fluid container 12 and prevent spillage of the contents. The cap 34 can be made of a material that has similar properties to that of the fluid container 12, e.g. sufficient mechanical strength and compatibility with the fluid. The cap 34 can also be formed as an integral part of the fluid container 12. Optionally, the cap can also contain self-sealing ports through which the fluid and/or additional material, such as stimuli, can be introduced. In one embodiment, fluid can be introduced through an inlet line 36, or through depositing the fluid into the fluid container 12 prior to securing the cap 34. The inlet line 36 can be configured as shown in FIG. 1A, or can be an aperture (not shown) in the wall of the fluid container. Optionally, the inlet can be in an opening on a disruption member, as shown in with respect to disruption member 14c (inlet line 18). In an alternative embodiment, a volume of fluid in excess of what is desired can be dispensed into the container, such that when the cap 34 is placed on the fluid container 12, a portion of the medium overflows out of the container 12 to achieve the desired volume of medium inside the container 12. Alternatively, the fluid container 12 can be pre-evacuated for a specific volume so that the platelet suspension or other fluid can be drawn into the container 12 by vacuum for the desired volume.

In another aspect of the present invention, a property measuring device 32 can be operatively associated with the measuring region. The property measuring device 32 can be a light scattering whole blood platelet aggregometer (LSWBPA), or another known light scattering device, optical device, ultrasound, electro-magnetic device, or mechanical device.

The above-described device can be used to measure a variety of fluid properties such as, but not limited to, platelet and leukocyte aggregation, degree of coagulation, particle count, density, viscosity, temperature, hematocrit, chemical composition, fluorescence, refractive index, absorption, attenuation, elasticity, compressibility, dielectric strength, impedance, echogenecity, specific heat, heat conductivity, osmolarity, diffusivity, and/or pH. A currently recognized use of the present invention is in the measurement of platelet aggregation of blood component-containing fluids. In this embodiment, the blood component-containing fluid can be introduced into the fluid container 12 through inlet 36 (or inlet 18). A stimulus, such as an aggregating agent, can be introduced into the blood component-containing fluid, which can cause a change in the blood component-containing fluid properties. The desired fluid properties can be measured and recorded using the property measuring device 32, which is typically operatively associated with the measuring region 28 of the fluid. Additionally, a baseline measurement of the property of interest can be taken prior to or shortly after introduction of the stimulus in order to quantify the effect of the stimulus on the fluid. The fluid container 12 with its contents can then be disposed of or recycled for future use.

Figure 1B:
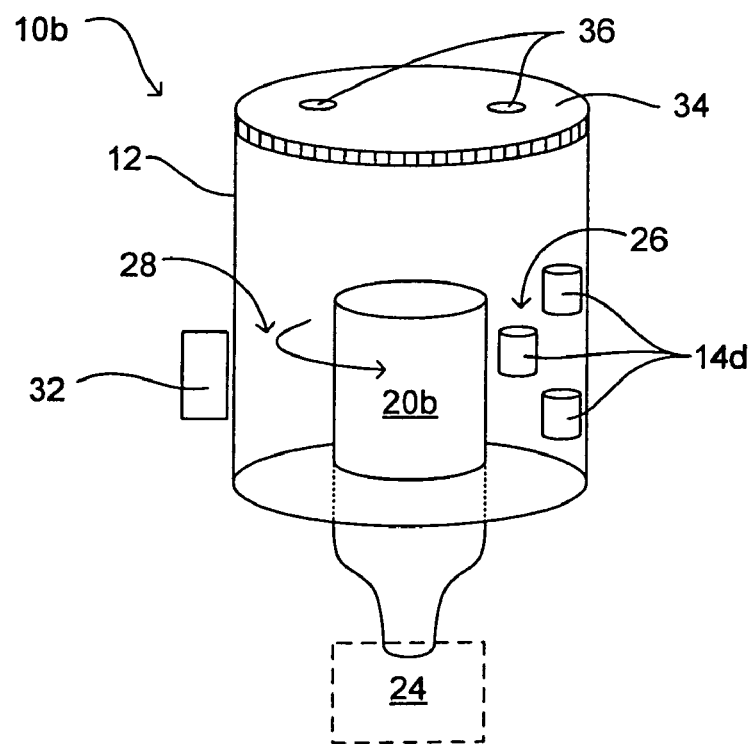
FIG. 1B is a perspective view of a fluid measurement device in accordance with another embodiment of the present invention showing alternative rotor and disruption members.

FIG. 1B depicts an alternative embodiment, illustrated generally at 10b, wherein a series of baffles 14d are used to provide separated flow in the mixing region 26. Additionally, the rotor 20b has a flat top and can be controlled by a motor 24 that is positioned below the container 12. Alternately, the rotor 20b can be controlled by a rotating magnet positioned above or below (not shown). An alternative cap 34 is shown having two inlets 36 and no shaft aperature, though more or less inlets can be present. Again, a light scattering device 32 is shown in operative communication with a measuring or streamlined flow region 28. Embodiments of the present invention utilizing this or other rotor-induced motion devices in the fluid can create low shear stresses into the fluid. At appropriate rotation speeds, this or other similar configuration can provide mixing and streamlined flow without causing significant damage to the fluid and particulates, such as platelet aggregates, and does not detrimentally alter the properties of the fluid.

Regarding the above and other embodiments, with respect to the stimulus that can be used, the stimulating agent that is introduced into the fluid to elicit response can be mechanical, electromagnetic, biological, chemical, or other stimulus. For example, in a platelet suspension, the platelets in the fluid container can be subjected to certain fluid dynamic forces in order to activate them via mechanical stimulus. Alternatively, the fluid can be subjected to electromagnetic stimulus using an electromagnetic field to elicit a response. In yet another alternative embodiment, the fluid can be subjected to biological agents such as bacteria, viruses, other platelets or white cells, or similar agents that cause a measurable biological response in the fluid. The response to the stimulus is usually the aggregation, agglutination, coagulation, or other types of clumping of the platelets within the fluid. Although introduction of a single stimulus is usually sufficient, several stimuli can also be introduced either simultaneously or sequentially. A pre-stimulus baseline measurement of the platelet suspension can be established while flow is induced in the fluid inside the container at an initial time prior to introducing the stimulus.

Specific stimuli that can be used for specific types of fluid are included by way of example, as follows. If a platelet-containing fluid is being used to measure platelet function, various activating/aggregating agents can be used alone or in combination, including adenosine di-phosphate (ADP), collagen, thrombin, epinephrine, ristocetin, calcium ionophore, thrombin receptor agonist protein (TRAP), arachidonic acid, and combinations thereof. If leukocyte function is to be measured, to a leukocyte-containing fluid can be added effective amounts of a leukocyte aggregating agent. Such leukocyte aggregating agents can include calcium ionophore, formyl-methyl-l-phenylalanine, or combinations thereof. Plasma or blood activating agents can include thrombin, diatomaceous earth, kaolin, celite, glass particulates, trypsin, pepane, phospholipids, or combinations thereof.

In keeping with the present invention, there are several mechanisms by which the stimulus can be introduced into the fluid. Chemical and/or biological stimuli can be injected into the fluid by a pipette, a needle, or other types of injection devices. Alternatively, the stimulus can be pre-dispensed onto an interior surface (e.g. by coating) within the container such as a disruption member, baffle, rotor, or inner surface of the container. In keeping with the present invention, the stimulus can also be dispensed into the fluid container prior to the introduction of the fluid into the container, in which case, a baseline can be quickly established before the onset of the response. In yet another optional embodiment, the stimulus can be introduced into the fluid after placing the fluid into the container.

The fluid response can be measured as the fluid components react to the stimulus. Such a response can be a change in viscosity, luminescence, conductivity, or other properties of the fluid. For example, with platelet containing fluids, the measured response is the number of the platelet aggregates of a minimum size as they form and disintegrate. The size of these platelet aggregates can also be measured as another type of response. Other combinations of number and size can also be measured. Further, an overall change in scattered light can be measured to reflect a change in bulk properties. These responses are recorded and subsequently analyzed so as to assess the functions of the platelet under investigation. At the conclusion of the test the fluid and the fluid container can be discarded. Alternatively, parts of the apparatus can be salvaged and recycled. The process of the present invention can also be considered essentially a batch process or closed system for the period between introduction of the stimulus and the final measurement of the target property.

Turning now to FIGS. 2A, 2B, and 2C, various alternative rotor configurations are shown, though other configurations can also be suitable for use. FIG. 2A shows a rotor 20c which includes two disk shaped members connected by a shaft. The fluid to be mixed and measured can be present between the two disks. A disturbing member (not shown) can be between the two disks of the rotor 20c, providing separated flow in a mixing region. The rotor 20c may or may not leave sufficient space between the disk edges and the inner surface 16 of the fluid container 12 to allow fluid to flow therethrough.

FIG. 2B shows another alternative rotor 20d that includes a single disk connected to a shaft. The rotor 20d may or may not leave sufficient space between the disk edges and the inner surface 16 of the fluid container 12 to allow fluid to flow therethrough.

FIG. 2C shows yet another alternative rotor 20e including a generally cylindrical member having a conical shape at each end. The length of the rotor 20e can correspond roughly to the height of the fluid container 12, such that the points 21 of the rotor 20e correspond to and couple with associated cavities or other retaining members (not shown) on the inner surface 16 of the fluid container 12 or cap (not shown). Rotor 20e can include a magnetically responsive element formed inside the rotor so as to enable rotation based on a magnetic field similar to the operation of a magnetic stir bar. Typically, a rotor having a cylindrical or conical shape provides good flow results and is relatively simple to manufacture.

Other suitable shapes for use in the rotor aspect of the present invention include, but are not limited to, spherical, elliptical, quadrilateral, and combinations of these shapes. Alternatively, flow of the fluid can be induced using magnetic stir bars or other known mixers that produce a measuring region suitable for use in the present invention. A variety of methods can be employed to induce flow in the fluid consistent with the methods of the present invention. Suitable methods for platelet-containing fluids will expose the fluid to relatively low shear stresses and minimize and/or avoid damage to fluid components. Alternatively, the rotation can be powered by electromagnetic force. If the rotor is driven electromagnetically, a magnetic stir bar could be used or a bar made of magnetic material such as iron would be embedded within the rotor.

In FIG. 3, several non-limiting examples of various disruption members having a variety of shapes and contours are shown. Each of the disruption members 14 shown, as well as others, can include simple straight rods, magnetic stir bars, baffles, more complex fin-like designs, unattached vagile objects, or other means for mixing the fluid.

Figure 4A:
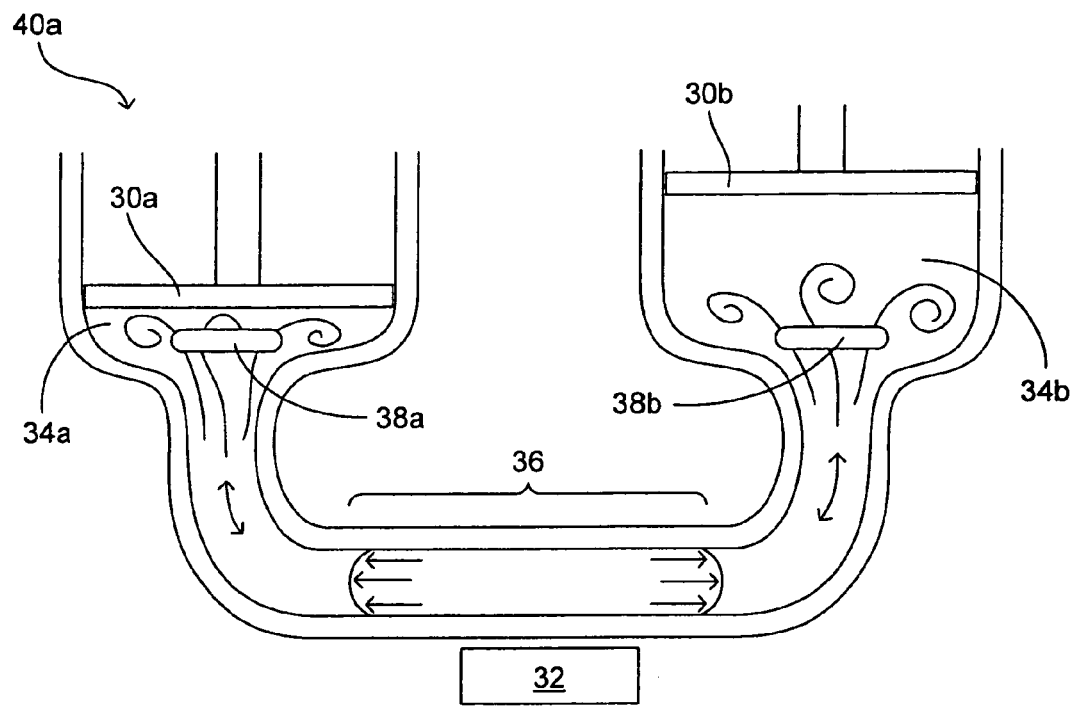
FIGS. 4A and 4B illustrate cross-sectional views in accordance with a forced flow embodiment of the present invention.
Figure 4B:
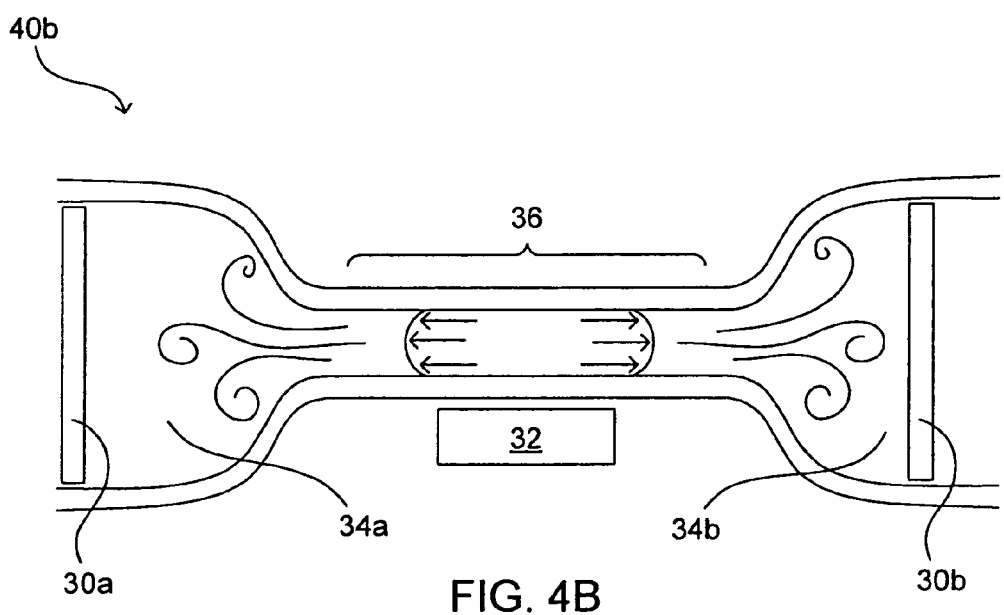

In an alternative embodiment of the present invention, flow of the fluid can also be induced using forced flow. FIGS. 4A and 4B illustrate forced flow configurations in accordance with principles of the present invention. Specifically, two similar embodiments, illustrated generally at 40a and 40b, respectively, show two mixing regions 34a and 34b connected by an elongated streamline flow path or measuring region 36. The fluid is forced from mixing region 34a toward mixing region 34b via flow path 36 using pistons 30a and 30b. As piston 30a moves toward the flow path 36, fluid is mixed in mixing region 34a, and is further mixed as the fluid exits the measuring region 36 and enters mixing region 34b. During this movement, piston 30b moves away from the measuring region 36 to increase the volume of mixing region 34b. Following the completion of this forced flow in one direction the process is reversed by moving piston 30b toward the measuring region 36 and forcing the fluid back to the left along measuring region 36. Though two pistons are shown and described, the presence of two pistons is not required. This effectuates mixing in each of the mixing regions 34a and 34b. The measuring region 36 provides streamlined flow suitable for use in the present invention using measurement device 32, as in previously described embodiments. In this embodiment of the present invention, the flow recirculates through the apparatus in a bi-directional manner, e.g. the fluid in the measuring region traverses the same path in alternating flow directions.

In addition to that described above, the mixing regions can take various shapes and dimensions consistent with the methods of the present invention. For example, a region of narrowing geometry in the mixing region, where the mixing region begins to narrow toward the measuring region 36, is an area of vortex formation. There, sufficient mixing can occur to facilitate aggregation and homogenization of the fluid. The region of converging geometry is also an area where there are significant inter-platelet collisions, which also aids aggregation and accurate measurement. Stir bars 38a, 38b can also be incorporated in the narrowing areas of the reservoirs to further enhance mixing if desired, as shown in FIG. 4A. The elongated measuring region 36 is a region where there is streamlined flow that facilitates detection of aggregation or other fluid properties, especially by light scattering as discussed above. The elongated measuring region 36 can be made of materials similar to that of the mixing regions 26a and 26b. Preferably, at least a part of the conduit must permit passage of electromagnetic signals. If this embodiment were to be used with a LSWBPA, at least a portion of the flow path would be transparent to light. The interface between the piston and the wall of the mixing regions will generally form a seal and be substantially impermeable to the fluid.

In another aspect of the present invention, streamlined flow can be induced in a fluid by an external drive, such as by rotating the fluid container while holding a rotor stationary (or rotating at a different rate or direction), or by otherwise moving the fluid container to cause fluid flow having the above described characteristics of a mixing and a measuring region within the container.

Figure 5A:
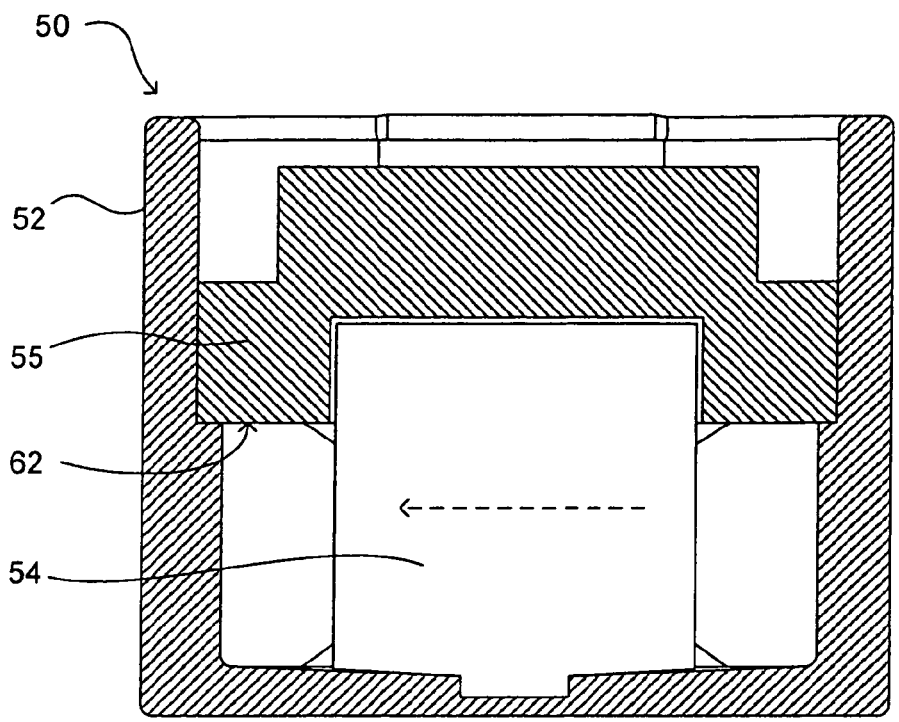
FIG. 5A is a cross-sectional view of a fluid property measurement system having a stenotic baffle system in accordance with an embodiment of the present invention.

In yet another aspect of the present invention consistent with the above description, FIG. 5A shows a fluid property measurement system 50. A fluid container 52 can include a fluid movement device such as a rotor 54 positioned within the fluid container. The fluid movement device can be configured to produce flow of fluid within the container along a desired fluid flow path, e.g., causing circumferential recirculation. In the case of FIG. 5A, the fluid flow path is an annular recirculating flow as the rotor spins within the fluid container. A cap 55 can be configured to fit over the rotor within the fluid container as shown to provide a seal and to prevent loss or contamination of the contents during use. The fluid container and cap can optionally include threaded surfaces to allow mating of the two pieces. Alternatively, the cap can be secured via an interference fitting, latch, snap, adhesive, seal, and/or other similar mechanism.

Figure 5B:
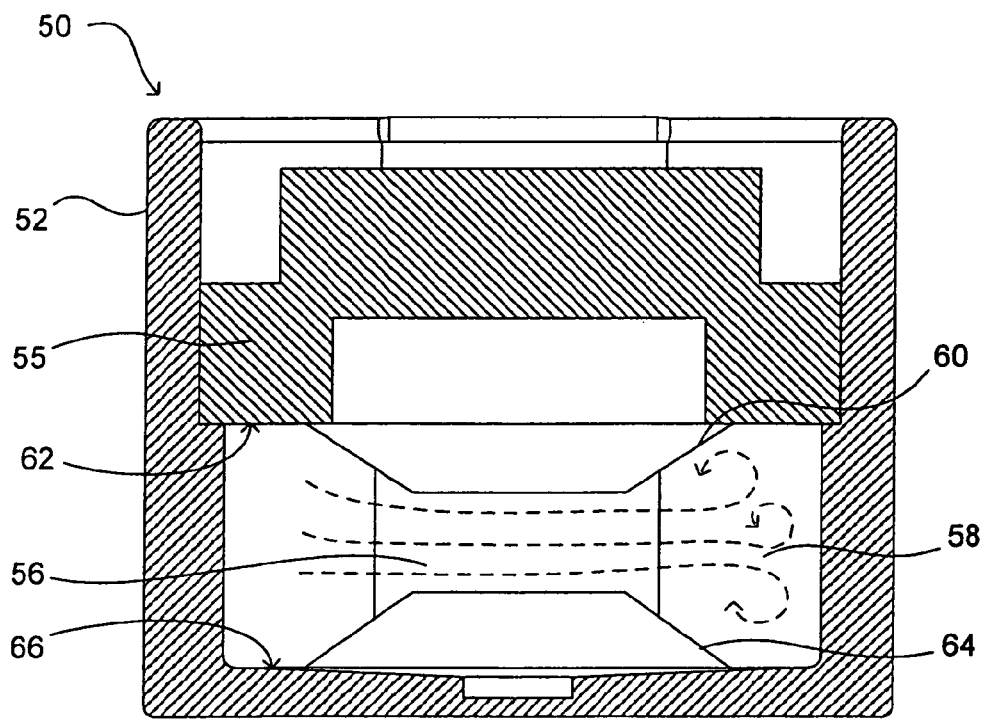
FIG. 5B is a cross-sectional view of the embodiment shown in FIG. 5A having the rotor removed.

The measuring region can be a constricted region where fluid flow passes through a volume having a smaller cross-sectional area than neighboring volumes along the fluid flow path. FIG. 5B is a cross-sectional view of the system 50 of FIG. 5A having the rotor removed. A constricted region 56 can be formed which generates a region of streamlined flow within the constricted region, shown generally by three flow lines 57. Thus, the constricted region can cause the fluid to increase in velocity over a portion of the fluid flow path. An increase in fluid velocity can improve particulate measurement results based on light scattering. The constriction can also facilitate fluid dynamic focusing that concentrates particulates to be measured in the detection region. In addition, increased fluid velocity can reduce agglomeration or blockage of the fluid flow path. Such methods can benefit from increased resolution and decreased signal-to-noise ratio as fluid flow is increased. As the fluid exits the constricted region, at least some mixing occurs as the fluid expands outside of the constricted region into a mixing region 58. Advantageously, the constricted region and subsequent expansion that occurs in the mixing region thus acts to provide streamlined flow and mixing using a single feature, e.g., stenotic baffle. Such expansion mixing also achieves some of the purposes of the present invention by reducing damage to platelets and other fragile materials.

The constricted region shown in FIG. 5B is a stenotic baffle system including a top baffle 60, which in this embodiment is positioned on the cap 55 to form an upper streamlined flow surface for the constricted region 56. A bottom baffle 64 can also be formed along a lower inner surface 66 of the fluid container to form a lower streamlined flow surface of the constricted region. In the embodiment shown in FIG. 5B, though the top baffle is positioned on the cap, the top baffle can alternatively be attached to or formed as in integral part of the fluid container. It should be noted that though not necessary, a secondary disruption member such as those shown and described in connection with FIGS. 1A, 1B, and 3 can also be used in conjunction the stenotic baffle embodiment described herein. The secondary disruption member can be positioned anywhere except in the constricted region (as it would disrupt the streamlined flow), but is preferably positioned at or near the mixing region 58 following the streamlined stenotic baffle.

Figure 5C:
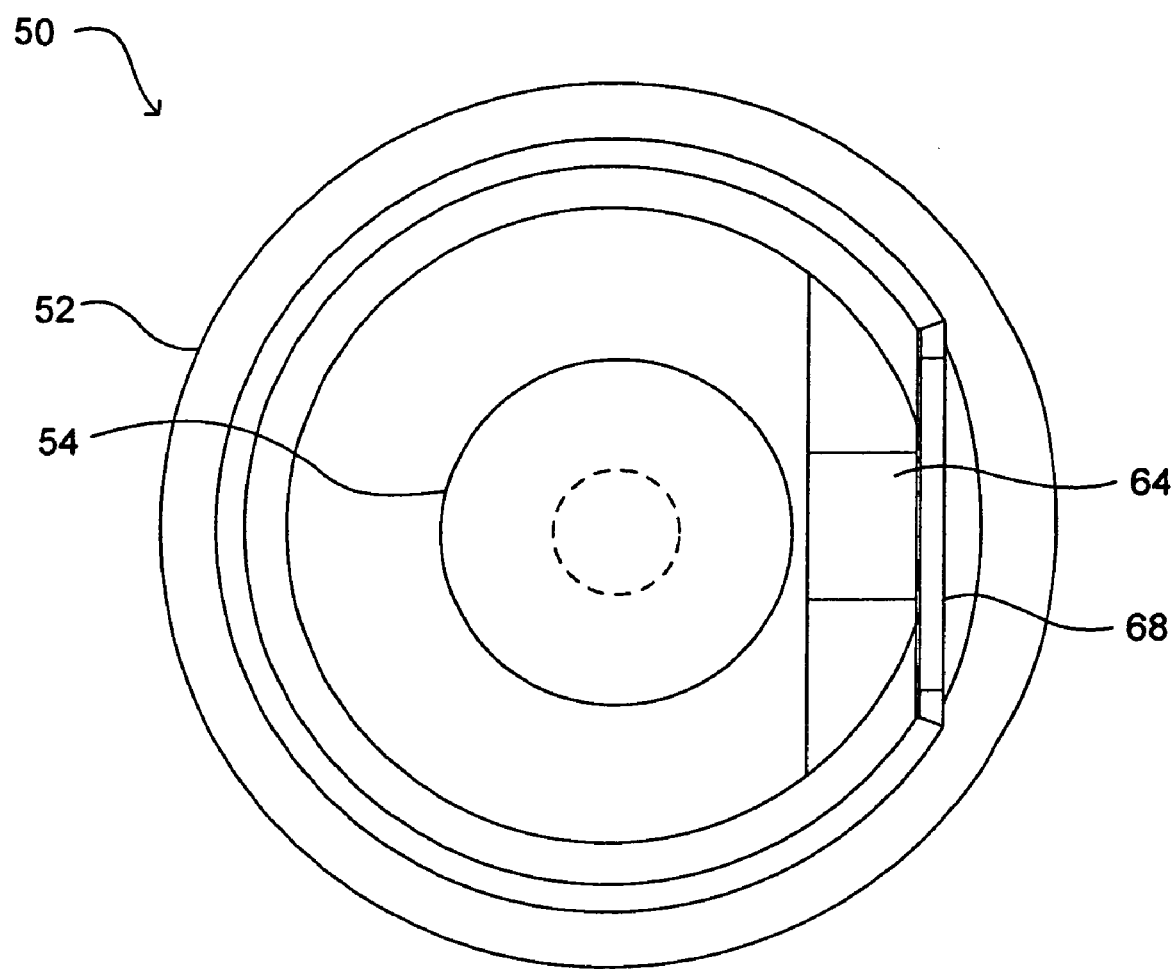
FIG. 5C is a top view of the embodiment shown in FIG. 5A having the cap removed.

FIG. 5C is a top view of the fluid property measurement system 50 having the cap removed. From this perspective, the bottom baffle 64 can be seen having a width which covers nearly the entire fluid path width. In one embodiment, the distance between the rotor and the baffles can be carefully chosen in order prevent damage to fluid which passes therebetween while also maximizing the constricting affect of the stenotic baffle system. Typically, the stenotic baffles system can have a width from about 50% to about 95%, and preferably about 75% to about 95% of the shortest distance between the inner wall and the rotor. Further, the bottom baffle can be oriented adjacent a light transparent window 68 which is also placed along at least a portion of the constricted region. The constricted region, or measuring region, can allow the light transparent window to be used for measurement of aggregation or other particulates via light scattering devices or other property measurement devices as described above. The light transparent window can alternatively be translucent, as long as the wavelength of light used can pass through the window functionally. The constricted region can alternatively be formed by using a single stenotic baffle. In yet another aspect of the present invention, the constricted region can be formed having conically fluted entrance and exit points. In one embodiment, the baffle or baffle assembly design can produce three dimensional velocity vectors that result in radial, circumferential, and/or vertical mixing.

In each of the embodiments described above, the fluid container includes a region(s) where the local flow patterns of the fluid are such that there is substantial mixing of the fluid. Further, the fluid container includes another region(s) separate from the mixing region(s) where the flow characteristics are substantially streamlined. Such streamlined flow is steady enough that the entities of interest in the fluid, e.g. platelet aggregates in a blood component-containing fluid, carried in it can be detected more accurately by certain detection methods, such as light scattering. As recirculation occurs in the measuring region, a more complete sample of fluid can also be measured. Moreover, the above mixing and streamlined flow characteristics are induced using methods that minimize damage to, or alteration of entities of interest, e.g., platelet aggregates and coagulated masses. In addition, the present invention can be incorporated into a compact, disposable, and ergonomic design that further enables more reliable assessments of platelet function.

Further, the systems and devices of the present invention are designed to measure of free stream particulates such as platelet aggregates. The fluid flow velocity, disruption member designs such as constricted regions or baffles, and other variables can be adjusted to encourage aggregation of platelets while in the fluid rather than impact and agglomeration on an interior surface of the device. For example, a relatively high shear rate, e.g. $200\ s^{-1}$ to $2000\ s^{-1}$ can be maintained in order to prevent platelet aggregates from adhering to walls or baffles. Thus, in one embodiment, the systems of the present invention can measure free stream aggregation with significantly reduced concerns and affects associated with clogging and blockage which can occur as masses of material build up on moving parts or other surfaces.

EXAMPLES

The following examples illustrate embodiments of the invention that are presently known. Thus, these examples should not be considered as limitations of the present invention, but are merely in place to teach how to make the best-known systems and methods of the present invention based upon current experimental data. As such, a representative number of systems and methods are disclosed herein.

Example 1

A cylindrically shaped fluid container having an inner diameter of 11 mm, a height of 20 mm, and a wall thickness of 2 mm was obtained. The fluid container is formed of a polycarbonate, coated on the inner surface with a non-tacky coating to increase compatibility with blood. A cylindrical cap, having an 11 mm inner diameter and 20 mm height made of the material DELRIN™ was fitted to substantially seal the inner diameter of the fluid container. The cap had a 4 mm diameter hole in the center, extending entirely through the height of the cap, i.e., 20 mm, and includes a side notch measuring 5 mm by 5 mm (also extending the entire length of the cap). The rotor included a cylindrical shaft 24 mm in length and 4 mm in diameter, and a rotor body that was 6 mm in diameter and 6 mm in length. The bottom of the rotor body included a sharp pointed tip with a 30° angle similar to rotor 20a shown in FIG. 1A. A disruption member was present that included a cylindrical protrusion measuring 3 mm in diameter and 2 mm in length, which was molded as part of the interior of the container wall. The disruption member was positioned 3 mm from the bottom of the side wall and had a cylindrical axis oriented along the radial direction of the container. This cylinder had a 45° bevel cut on the side facing the center of the container.

The apparatus was then used to measure platelet aggregation of whole blood as follows: Blood (0.2 ml) was injected into the fluid container. A rotational speed of about 600 RPM was set for the rotor. A differential light-scattering detector was positioned externally on a side opposite the disruption member. A blood baseline was measured with the detector for a period of 5 seconds to set the platelet aggregate threshold. After the measurement of the baseline and the establishment of the threshold, a platelet-aggregating agent of 10 µl ADP solution was injected into the moving blood resulting in a final concentration of ADP in blood of 50 µM. Platelet aggregates formed under the stimulation of the ADP and the flow and mixing induced by the rotor and disrupting member. In regions opposite the mixer, i.e., the streamlined flow or measuring region, where the detector was located, the blood flow is essentially streamline. Hence, the detector measured the platelet aggregates that were entrained inside the blood flow as distinctive spiked signals above or below the baseline. As these signals developed beyond the threshold, they were recorded. After 2 minutes of measurement, the recording was terminated and the entire fluid container with the blood inside was discarded.

Example 2

A fluid container including two identical reservoirs connected by an elongated conduit was formed, similar to the embodiment shown in FIG. 4A. The base of each reservoir was 20 mm in diameter and the length of each reservoir was 30 mm. At 20 mm below each base, the diameter gradually decreased to 3 mm at the top. The reservoirs were made of polypropylene, coated with a non-adhesive coating to increase blood compatibility. At the base of each reservoir was a piston that was 20 mm in diameter and 10 mm in length. The movement of the piston up and down into each respective reservoir was propelled by a linear actuator. The narrow ends of the reservoirs were connected with a conduit of polyvinyl chloride tubing having a 3 mm inner diameter, a 1.5 mm wall thickness, and 40 mm length. One reservoir contained a 2 mm circular injection port and a self-sealing rubber diaphragm 5 mm from the top.

A volume of 1 ml of whole blood was transferred into one of the two reservoirs prior to attachment of the piston. The piston was then attached to the base of that reservoir to seal in the blood. The two pistons were moved up and down oppositely in synchrony so that the blood was transferred between the two reservoirs through the conduit. Average flow velocity inside the conduit was 20 mm per second. After the establishment of the baseline and threshold, a platelet-aggregating agent was injected into one reservoir through the self-sealing diaphragm port. Under the stimulation of the agent and with the help of the mixing brought on by the contraction-expansion of blood flow, platelet aggregates formed inside the sample holder. As these platelet aggregates were carried by the blood through the conduit, they were measured by a detector placed along the conduit and recorded. After 2 minutes of measurement, the recording was stopped, and the whole sample holder was retrieved for recycling.

Example 3

A cylindrically shaped fluid container having an inner diameter of 10 mm, a height of 8 mm, and a wall thickness of 1 mm was obtained. The fluid container is formed of a polycarbonate, coated on the inner surface with a non-tacky coating to increase compatibility with blood. A cylindrical cap, having a 10 mm inner diameter and 4 mm height made of the material DELRAN™ was fitted to substantially seal the inner diameter of the fluid container. The rotor included a cylindrical shaft 24 mm in length and 4 mm in diameter, and a rotor body that was 6 mm in diameter and 6 mm in length. The bottom of the rotor body included a plug tip which fit into a recess in the bottom of the fluid container similar to rotor 54 shown in FIG. 5A. A stenotic baffle system was present that included a top baffle having a total length of 7 mm, inclined portions over 2 mm at a 60° incline, and a flat lower portion having a length of 3 mm. A corresponding lower baffle was formed having the same dimensions as the top baffle. Each stenotic baffle of the assembly was about 3 mm wide at their center and the annular space between the rotor and inner walls was about 1.5 mm. The stenotic baffles were formed of polycarbonate and DELRAN™. A transparent window measuring 3 mm by 3 mm is formed as part of the fluid container wall adjacent the stenotic baffle system.

The apparatus was then used to measure platelet aggregation of whole blood as follows: Blood (0.2 ml) was placed into the fluid container. A rotational speed of about 600 RPM was set for the rotor. A differential light-scattering detector was positioned externally on a side opposite the disruption member. A blood baseline was measured with the detector for a period of 3 seconds to set the platelet aggregate threshold. After the measurement of the baseline and the establishment of the threshold, a platelet-aggregating agent of 0.2 mM solution was injected into the moving blood resulting in a final concentration of ADP in blood of 10 µM. Platelet aggregates formed under the stimulation of the ADP and the flow and mixing induced by the rotor and constricting region. In the constricting region, the streamlined flow or measuring region, where the detector was located, the blood flow is essentially streamline. Hence, the detector measured the platelet aggregates that were entrained inside the blood flow as distinctive spiked signals above or below the baseline. As these signals developed beyond the threshold, they were recorded. After 2 minutes of measurement, the recording was terminated and the entire fluid container with the blood inside was discarded.

The above description and examples are intended only to illustrate certain potential uses of this invention. It will be readily understood by those skilled in the art that the present invention is susceptible of a broad utility and applications. Many embodiments and adaptations of the present invention other than those herein described, as well as many variations, modifications, and equivalent arrangements will be apparent from or reasonably suggested by the present invention and the forgoing description thereof without departing from the substance for scope of the present invention. Accordingly, while the present invention has been described herein in detail in relation to its preferred embodiment, it is to be understood that this disclosure is only illustrative and exemplary of the present invention and is made merely for purpose of providing a full and enabling disclosure of the invention. The forgoing disclosure is not intended or to be construed to limit the present invention or otherwise to exclude any such other embodiment, adaptations, variations, modifications and equivalent arrangements, the present invention being limited only by the claims appended hereto and the equivalents thereof.

What is claimed is:

1. A fluid property measurement system for measuring free stream particulates, comprising:
   a) a fluid movement device configured to cause bi-directional forced fluid flow within a fluid container along a fluid flow path when a fluid is present in the fluid container;
   b) a constricted region along the fluid flow path which subjects the fluid within the container to a region of concentrated streamlined flow within the constricted region and mixing of the fluid outside of the constricted region; and
   c) a property measuring device positioned with respect to the constricted region to measure fluid properties in the region of streamlined flow.

2. The fluid property measurement system as in claim 1, wherein the fluid is present in the system and is selected from the group consisting of blood, platelet suspension, leukocyte suspension, red blood cell suspension, plasma, and combinations thereof.

3. The fluid property measurement system as in claim 1, wherein the fluid is present in the system and further comprises a stimulating agent.

4. The fluid property measurement system as in claim 3, wherein the stimulating agent is an aggregating agent.

5. The fluid property measurement system as in claim 3, wherein the stimulating agent is dispensed into the fluid container after the fluid has been dispensed into the fluid container.

6. The fluid property measurement system as in claim 3, wherein the stimulating agent is dispensed into the fluid container before the fluid has been dispensed into the fluid container.

7. The fluid property measurement system as in claim 3, wherein the stimulating agent is combined with the fluid to form a mixture before the mixture is introduced into the fluid container.

8. The fluid property measurement system as in claim 3, wherein the stimulating agent and the fluid are introduced simultaneously into the fluid container.

9. The fluid property measurement system as in claim 3, wherein the stimulating agent is selected from the group consisting of gases, liquids, solids, and combinations thereof.

10. The fluid property measurement system as in claim 1, wherein the fluid is present in the system and contains exogenous additives.

11. The fluid property measurement system as in claim 1, wherein the fluid movement device is a pair of plungers positioned at opposing ends of the fluid container.

12. The fluid property measurement system as in claim 1, further comprising a secondary disruption member which contributes to mixing of the fluid.

13. The fluid property measurement system as in claim 12, wherein the secondary disruption member is an obstruction attached to or on an inner surface of the fluid container.

14. The fluid property measurement system as in claim 1, wherein the property measuring device is based on light scattering.

15. The fluid property measurement system as in claim 1, wherein the constricted region causes the fluid to increase in velocity over a portion of the fluid flow path.

16. The fluid property measurement system as in claim 1, wherein the constricted region, when in operation, causes the fluid to become dynamically focused within the constricted region.

17. The fluid property measurement system as in claim 1, wherein the container is evacuated.

18. The fluid property measurement system as in claim 1, wherein the constricted region is formed by a stenotic baffle system.

19. The fluid property measurement system as in claim 18, wherein the stenotic baffle system includes a top baffle along an inner surface of the fluid container or along a cap on the fluid container to form an upper streamlined flow surface in the constricted region and a bottom baffle along a lower inner surface of the fluid container to form a lower streamlined flow surface in the constricted region.

20. The fluid property measurement system as in claim 1, wherein the constricted region facilitates fluid dynamic focusing that concentrates particulates to be measured in the region of concentrated streamlined flow.

21. The fluid property measurement system as in claim 1, wherein the constricted region and fluid movement device are configured to provide free stream aggregation of material.

22. A method for measuring properties of a fluid, comprising the steps of:
   a) placing a quantity of fluid in a container;
   b) inducing bi-directional forced flow in the fluid with a fluid movement device, wherein the flow is substantially streamlined in at least a measuring region of the container by constricting flow, and wherein the fluid is recirculated through the measuring region by the bi-directional forced flow;
   c) creating a mixing region separate from the measuring region of the container sufficient to substantially mix the fluid, said mixing region generated by expanding flow of the fluid from the constricted flow of the measuring region; and
   d) measuring a property of the fluid in the measuring region.

23. A method as in claim 22, further comprising the step of introducing a stimulus to the fluid prior to measuring a property of the fluid.

24. A method as in claim 23, further comprising the step of measuring the property of the fluid at an initial time prior to introducing the stimulus.

25. A method as in claim 23, wherein the stimulus is selected from the group consisting of an aggregating agent, mechanical stimulus, biological stimulus, chemical stimulus, and combinations thereof.

26. A method as in claim 22, wherein the steps of inducing flow and creating a mixing region do not detrimentally alter the properties of the fluid.

27. A method as in claim 22, wherein the fluid is selected from the group consisting of blood, platelet suspension, leukocyte suspension, red blood cell suspension, plasma, and combinations thereof.

28. A method as in claim 22, wherein the fluid is a non-physiological fluid.

29. A method as in claim 22, wherein the step of inducing flow and creating the mixing region occur under conditions such that free stream aggregation of material occurs.

30. A method as in claim 22, wherein the step of creating the mixing region is accomplished by a stenotic baffle system.

31. A method as in claim 22, wherein steps a)-d) are performed sequentially.

32. A method for measuring platelet aggregation, comprising steps of:

a) placing a quantity of fluid in a container wherein the fluid includes a blood component and an aggregating agent;
b) inducing bi-directional forced flow in the fluid with a fluid movement device positioned in the container, wherein the flow is substantially streamlined in at least a measuring region of the container by constricting flow, and wherein all of the fluid is recirculated through the measuring region by the bi-directional forced flow;
c) creating a mixing region separate from the measuring region sufficient to substantially mix the fluid and contribute to free stream aggregation of the blood component, said mixing region generated by expanding flow of the fluid from the constricted flow of the measuring region; and
d) measuring platelet aggregation of the fluid in the measuring region using a light scattering device.

33. A system for measuring properties of a fluid, comprising:
a) a fluid container;
b) means positioned with respect to the container for inducing bi-directional forced flow in a fluid present within the container, wherein the flow is substantially streamlined in at least a measuring region of the container by constricting flow, and wherein the fluid is recirculated through the measuring region by the bi-directional forced flow;
c) means for creating a mixing region separate from the measuring region, sufficient to substantially mix the fluid, said mixing region generated by expanding flow of the fluid from the constricted flow of the measuring region; and
d) a property measuring device operatively associated with the measuring region.

34. A system as in claim 33, wherein the means for creating the mixing region is a stenotic baffle system affixed to an inner surface of the container.

35. A system as in claim 33, wherein the fluid is selected from the group consisting of blood, platelet suspension, leukocyte suspension, red blood cell suspension, plasma, and combinations thereof.

36. A fluid property measurement system for measuring free stream particulates, comprising:
a) a pair of plungers positioned at opposing ends of a fluid container configured to cause bi-directional forced fluid flow within the fluid container along a fluid flow path when a fluid is present in the fluid container;
b) a constricted region along the fluid flow path which subjects the fluid within the container to a region of concentrated streamlined flow within the constricted region and mixing of the fluid outside of the constricted region; and
c) a property measuring device positioned with respect to the constricted region to measure fluid properties in the region of streamlined flow.

37. A fluid property measurement system for measuring free stream particulates, comprising:
a) a fluid movement device configured to cause bi-directional forced fluid flow within a fluid container along a fluid flow path when a fluid is present in the fluid container, wherein the fluid container is pre-evacuated;
b) a constricted region along the fluid flow path which subjects the fluid within the container to a region of concentrated streamlined flow within the constricted region and mixing of the fluid outside of the constricted region; and
c) a property measuring device positioned with respect to the constricted region to measure fluid properties in the region of streamlined flow.

38. A fluid property measurement system for measuring free stream particulates, comprising:
a) a fluid movement device configured to cause bi-directional forced fluid flow within a fluid container along a fluid flow path when a fluid is present in the fluid container;
b) a constricted region situated along the fluid flow path and formed by a stenotic baffle system that subjects the fluid within the container to a region of concentrated streamlined flow within the constricted region and mixing of the fluid outside of the constricted region; and
c) a property measuring device positioned with respect to the constricted region to measure fluid properties in the region of streamlined flow.

39. The fluid property measurement system as in claim 38, wherein the stenotic baffle system includes a top baffle along an inner surface of the fluid container or along a cap on the fluid container to form an upper streamlined flow surface in the constricted region and a bottom baffle along a lower inner surface of the fluid container to form a lower streamlined flow surface in the constricted region.

40. A method for measuring properties of a fluid, comprising the steps of:
a) placing a quantity of fluid in a container;
b) inducing bi-directional forced flow in the fluid with a fluid movement device, wherein the flow is substantially streamlined in at least a measuring region of the container by constricting flow, and wherein the fluid is recirculated through the measuring region by the bi-directional forced flow;
c) creating a mixing region separate from the measuring region of the container sufficient to substantially mix the fluid, said mixing region generated by expanding flow of the fluid from the constricted flow of the measuring region, wherein the mixing region is created with a stenotic baffle system; and
d) measuring a property of the fluid in the measuring region.

41. A system for measuring properties of a fluid, comprising:
a) a fluid container;
b) means positioned with respect to the container for inducing bi-directional forced flow in a fluid present within the container, wherein the flow is substantially streamlined in at least a measuring region of the container by constricting flow, and wherein the fluid is recirculated through the measuring region by the bi-directional forced flow;
c) a stenotic baffle system affixed to an inner surface of the fluid container and configured to create a mixing region separate from the measuring region, sufficient to substantially mix the fluid, said mixing region generated by expanding flow of the fluid from the constricted flow of the measuring region; and
d) a property measuring device operatively associated with the measuring region.

* * * * *